United States Patent [19]

Sanders

[11] 4,171,350

[45] Oct. 16, 1979

[54] METHOD FOR REACTING HYDROGEN AND OXYGEN IN THE PRESENCE OF A LIQUID PHASE

[75] Inventor: Frederick W. Sanders, Chillicothe, Ohio

[73] Assignee: The Mead Corporation, Dayton, Ohio

[21] Appl. No.: 930,707

[22] Filed: Aug. 3, 1978

Related U.S. Application Data

[63] Continuation of Ser. No. 265,975, Jun. 26, 1972, abandoned.

[51] Int. Cl.$^2$ .................................................. C01B 5/00
[52] U.S. Cl. .................................... 423/580; 423/219; 423/248; 176/37
[58] Field of Search ....................... 423/580, 219, 248; 176/16, 37

[56] References Cited

U.S. PATENT DOCUMENTS

| 2,459,907 | 1/1949 | Winslow et al. | 252/477 X |
| 3,023,085 | 2/1962 | McBride | 423/580 |
| 3,666,405 | 5/1972 | Winsel | 423/229 |
| 3,681,021 | 8/1972 | Mikovsky et al. | 423/580 |
| 4,024,229 | 5/1977 | Smith | 423/562 |

Primary Examiner—Earl C. Thomas
Attorney, Agent, or Firm—Biebel, French & Nauman

[57] ABSTRACT

The rates of reaction between two gases is controlled by bringing the gases (hydrogen and oxygen) into an aqueous medium and into contact with a Contacogen which is wetproofed with respect to the medium. Even if the reaction between the gases in gas phase is exothermic, then normally the rate is quite slow if the reaction is carried out in a liquid such as water. By the use of a Contacogen, the rate is increased substantially over that in which the gases are reacted in a liquid medium, and much controlled over that which takes place in a gas phase reaction. The Contacogen is particulate in nature and maintained in a static condition and forms the situs of reaction between the two gases in the presence of an aqueous medium, the latter normally tending to inhibit reaction. The Contacogen is wetproofed to prevent flooding thereof by the aqueous medium and operates to increase the rate of reaction between the gaseous reactants in the aqueous medium over that possible absent the Contacogen.

3 Claims, No Drawings

METHOD FOR REACTING HYDROGEN AND OXYGEN IN THE PRESENCE OF A LIQUID PHASE

CROSS REFERENCE TO RELATED APPLICATIONS

This is a continuation of application Ser. No. 265,975, filed June 26, 1972, and now abandoned.

Reference is made to application Ser. No. 87,503, filed Nov. 6, 1970, now abandoned in favor of continuation-in-part application Ser. No. 356,569, filed May 2, 1973, which in turn has been abandoned in favor of continuation application Ser. No. 517,246, fild Oct. 23, 1974 and now U.S. Pat. No. 4,054,419; application Ser. No. 87,504, filed Nov. 6, 1970, now abandoned in favor of continuation application Ser. No. 468,471, filed May 9, 1974 and now U.S. Pat. No. 4,024,229; and Ser. No. 206,127, filed Dec. 18, 1971, now U.S. Pat. No. 3,927,111; Ser. No. 230,525, filed Feb. 29, 1972, now abandoned in favor of Ser. No. 481,778, filed June 21, 1974 and now U.S. Pat. No. 4,001,385; and Ser. No. 252,285, filed May 11, 1972, now U.S. Pat. No. 3,849,278, all assigned to the same assignee as the present invention.

BACKGROUND OF THE INVENTION

The present invention relates to gas-gas reactions and more particularly to an improved system for carrying out gas-gas reactions and for controlling the rate thereof. Specifically, the present invention relates to an improved method for controlling the rate of reaction between gaseous reactants in the presence of a liquid medium.

The rate of highly exothermic reactions between reactants in the gas phase is frequently so rapid as to be explosive, while carrying out the same reaction between gaseous reactants in the presence of a liquid, such as an aqueous medium, so reduces the rate of reaction as to make it of no practical value. By use of a Contacogen in accordance with the present invention, the rate of reaction in the presence of the liquid may be increased so that these slow reactions achieve a useful rate, thereby providing a means to avoid the explosive rate while accomplishing the desired reaction. The reaction between gaseous reactants normally carried out in the presence of a liquid, e.g., an aqueous medium, may also be substantially and usefully accelerated by use of a Contacogen in accordance with the present invention.

DESCRIPTION OF THE PRIOR ART

Canadian Pat. No. 700,933 of Dec. 29, 1964, describes an electrolytic system wherein the cathode is in the form of a porous carbon member through which air or oxygen is introduced, the purpose, according to said patent, being to effect reaction between the cathodic gas product and oxygen and thereby to convert the usual cathode to a fuel cell type cathode. Also disclosed by this Canadian patent is the use of a slurry of particulate solids in the catholyte, the slurry being freely movable in the catholyte to contact the cathode proper. When particulate solids are used in the catholyte, they may be graphite or carbon impregnated with a metal catalyst, or metal particles, the particulate material being small enough to form an aqueous slurry which when aerated allows for free and rapid contact of such particles with the cathode. In one form, the catholyte particles may be partially coated with a hydrophobic material such as tetrafluoroethylene, silicones, etc. The conductive particles are said to act as absorbents or collectors for oxygen admitted and hydrogen evolved in the cathodic portion of the cell, and are said to accept electrons upon contact with the cathode which dissipates as they move through the electrolyte with the formation of hydroxyl ions or other hydrogen-oxygen ions and ultimately water. The data presented in this Canadian patent indicates that the presence of particulate material as a slurry in the catholyte does not significantly improve the performance of the cell as compared with operation absent the slurry. Here reference is made to a comparison of 105 Ma at 1.67 v absent the slurry vs. 110 Ma at 1.8 with the slurry present.

It is known in the art that air or oxygen may be used to depolarize a cathode. U.S. Pat. No. 3,124,520 of Mar. 10, 1964, describes a porous graphite cathode in a caustic-chlorine diaphragm cell in which air or oxygen is introduced into the porous cathode for depolarizing the cathode. Also disclosed is a hydrogen anode, i.e., a porous anode into which hydrogen gas is introduced in order to react with the oxygen which may be released at the anode.

U.S. Pat. No. 3,218,562 of Nov. 23, 1965, also describes the "fuel cell reaction", that is, the introduction of oxygen at the cathode which is wetproofed and which has a potential applied thereto in order to effect reduction of the oxygen by acceptance of electrons and the formation of water by reaction with hydrogen ions in the catholyte. The cathode is a porous plate impregnated with platinum and wetproofed with polytetrafluoroethylene. In one form, the cell is operated as a fuel cell with a load connected between the anode and cathode and wherein the two electrodes are separated by an ion exchange membrane, olefinic gas being introduced into the anolyte. In another form the cell is electrolytic with hydrogen released at the cathode.

U.S. Pat. No. 3,147,203 of Sept. 1, 1964, which relates to the production of carbonyl compounds from olefin feed stock, describes a fuel cell system in which oxygen is introduced into the cathode and olefin fuel gas at the anode, with power being generated.

U.S. Pat. No. 3,216,632 describes a bipolar cell for use in electrolysis in which the bipolar electrode is vertically above the anode, with the cathode portion of the bipolar electrode facing the anode and the anode portion thereof facing the cathode electrode. Hydrogen produced at the lowermost cathode diffuses through the cathode portion of the bipolar electrode and combines with oxygen at the anode portion to form water. The hydrogen released at the cathode electrode is withdrawn.

U.S. Pat. No. 2,390,591 of Dec. 11, 1945, relating to an electrolytic system for the production of oxygen gas from caustic alkali or acid solutions describes introducing air into a porous carbon cathode for the purpose of depolarizing the same.

Reference is also made to U.S. Pat. No. 3,258,415 of June 18, 1966, which uses a porous cathode and in which the depolarizing gas, and the gas being measured, is oxygen.

SUMMARY OF THE INVENTION

The present invention relates to reactions between gaseous reactants, such as hydrogen and oxygen, and more specifically an improved system for reaction between gaseous reactants in which the rate of reaction is controlled by use of a Contacogen and wherein gaseous materials may be reacted in the presence of a liquid medium.

The Contacogen preferably is in the form of particulate material, wetproofed to prevent flooding thereof, is maintained in a static condition and simultaneously contacted by the reactants and a liquid medium and forms the situs of the reaction between the reactants.

The type of reaction conditions with which the present invention is concerned involves the contact, in the presence of a liquid phase, of oxidant and reductant gaseous reactants at an interface of the Contacogen and the gases and liquid, this contact being an essential aspect of the system of this invention. This contact is in contradistinction to intermixing of the reactants as bubbles of gas in a liquid, as by a difuser, and the reaction is carried out at that locus of contact between the liquid and gases, and the Contacogen. For the purpose of simplification, and to identify the process of this invention and the essential elements thereof, the term Contacogen, trademark of The Mead Corporation, assignee of the present invention, is used to mean the solid material which forms the locus of the interfacial contact for the gases and liquid and which should be simultaneously contacted by each of them to produce the desired reaction.

Since the reaction zone involves two or more gases, the Contacogen and a liquid, the Contacogen must be in contact with the gases and wetted by the liquid but not flooded by either. Wetted, as used here, means that the contact angle between the Contacogen and the liquid is low, e.g., less than about 90° and approaching zero. If the contact angle is high, e.g., greater than about 90° and approaching 180°, then the liquid will tend to draw away from the surface of the Contacogen, and the surface of the Contacogen is in effect in substantial contact only with the gases, that is, flooded by the gases. On the other hand, with the surface of the Contacogen readily wetted by the liquid, that is, with a contact angle approaching zero between the Contacogen surface and the liquid, the liquid will tend to cover the surface of the Contacogen, and the surface of the Contacogen is in effect in substantial contact only with the liquid, that is, "flooded" by the liquid. As a practical matter the primary source of flooding is the liquid medium present. One method of preventing flooding, usually by the liquid is by treatment of the Contacogen which is designated as "wetproofing." This adds to the Contacogen a minor proportion of an inert substance not wetted by the liquid, that is, the contact angle between this inert additive and the liquid is greater than about 90°.

The Contacogen in accordance with the invention, is a solid which is essentially inert with respect to the gases, the liquid, and the products in the sense that it is not attacked in that it is physically consumed or degraded. A material having a high surface-area-to-weight ratio is preferred because it furnishes greater interfacial contact. In addition, the Contacogen is structured to promote simultaneous contact with both the gases and liquid and may be in various physical forms to accomplish this purpose. In the case of a Contacogen in particulate form, the particles are structured to provide a large surface area, for example, the particles are individually non-porous solids of large surface area, or they be structured to form larger particles which are porous.

In the case of porous materials used as a Contacogen, it will be understood that neither the liquid nor the gaseous reactants need be forced through the pores of the Contacogen in the sense that a porous member is used as a diffuser to form small bubbles of one reactant which are in intermixing contact with the other reactant.

Various solid materials may be used as a Contacogen, and platinized carbon, activated carbon, and other platinized materials are preferred. Of the above materials, carbon and activated carbon appear to provide optimum performance because of the relatively large surface-area-to-weight ratio obtainable, as well as the degree to which carbon may be finely divided. Moreover, this is a readily available material which may be obtained in a wide variety of particle sizes and surface areas. Carbons from different sources often result in different reaction rates. These variations are easily determined by simple procedures. Typical of the carbons usable in accordance with the present invention are carbon black, furnace black, channel black or carbons prepared by known procedures from various sources, for example, wood, corn cobs, beans, nut shells, bagasse, lignin, coals, tars, petroleum residues, bones, peat and other carbonaceous material.

The particle size may vary from 9 millimicrons to relatively large size, e.g., one inch or more, and usually the carbon is supplied as a mixture of various particle sizes. The surface area of the carbonaceous material may vary from 3 square meters per gram to in excess of 950 square meters per gram, as characterized by gaseous absorption using the BET method.

Carbon may be wetproofed as follows:

Polytetrafluoroethylene (PTFE) in emulsion form is intermixed with particulate carbon in an amount of between 0.1% to 100% based on carbon solids. The mixture is heated to remove the vehicle and dispersing agent for the PTFE. For further description of Contacogen and wetproofing, reference is made to Ser. No. 87,504, filed Nov. 6, 1970, now abandoned in favor of continuation application Ser. No. 468,471, filed May 9, 1974, both of which disclose that: Another wetproofing method involves treating particulate carbon in the ratio of 1 gram of linear polyethylene per 10 grams of carbon. The polyethylene is dissolved in the ratio of 1 gram of polyethylene per 100 grams of hot toluene and poured over the carbon. After treatment, the carbon is heated at approximately 105° C. to evaporate the toluene. The particles are not uniformly repellent but most of them are sufficiently repellent to float from several hours to several days.

Using the procedure described above, particulate carbon may also be wetproofed with polystyrene, fluorocarbon resins, polyethylene emulsions, silicones, or other hydrophobic materials, by any suitable procedure that avoids complete encapsulation by hydrophobic materials impermeable to the reactants or products formed. Other materials which may be used are chlorotrifluoroethylene, prepolymerized silicone oils, and high vacuum silicone grease, for example.

Another procedure includes subliming a chlorinated paraxylylene dimer in a vacuum chamber and depositing the vapors on materials such as particulate carbon and porous sintered nickel, thereby forming a poly(chloro-p-xylylene), known as "parylene".

In the case of materials such as finely divided platinum in an asbestos matrix, wetproofing is accomplished by using a 1% solution of polyethylene in toluene, wetting the asbestos matrix with the solution, draining off excess liquid then drying in an oven to evaporate the toluene.

In another example, paraffin wax is used in an amount varying from ½ to 2 grams per 10 grams of particulate carbon. The paraffin is dissolved in a solvent such as hexane or toluene, the carbon introduced into the mixture, heated and the solvent thereafter evaporated. Cetyl alcohol may also be used and applied in the same way. Any one of paratoluene sulfonamide, polydichlorodifluoroethylene and octadecyl amine may also be used and applied by intermixing with the carbon and heating the mixture to cause the treating material to adhere to the carbon. Each of the above materials operates satisfactorily in the new systems.

The particulate carbon may be bonded by a carboxylated styrene-butadiene latex used in an amount of 5 grams of 25% solids dispersion per 10 grams of carbon. The resulting material is a sheet which may be supported at the interface or a sodium sulfide solution and air, the reaction being apparent by the formation of the yellow color characteristics of polysulfide. In another example, polyethylene was dissolved in toluene, the polyethylene being used in the ratio of 5 grams per 10 grams of granular carbon and the toluene removed by floating the mixture on boiling water. The result was a bonded product which was sufficiently porous to permit passage of the oxygen containing gas and sufficiently wetproofed to float.

It is known that the rate of very fast gaseous reactions are slowed considerably if such reactions are conducted in the presence of a liquid, e.g., water. Also in the case of the slower reactions, the presence of a liquid does not have any beneficial effect from the standpoint of reaction rate, and may even slow these reactions further.

By the present invention, a Contacogen is used in the presence of a liquid and the rate of reaction between hydrogen and oxygen gaseous reactants is increased (compared to those conducted in the presence of a liquid) to a usefully productive rate, while slowed over the gas phase reaction so that the highly exothermic reaction is controlled. In short, the very fast gas-gas reactions are slowed to a useful rate, while the relatively slow gas-gas reactions run in the presence of a liquid have their rate increased. The control of rate of reaction is by use of a Contacogen in the presence of a liquid.

Accordingly, it is a primary object of the present invention to provide an improved system for carrying out reactions between hydrogen and oxygen gaseous reactants in the presence of liquid and a Contacogen, the latter operating to increase the rate of reaction between the gaseous reactants in the presence of a liquid.

Another object of the present invention is the provision of an improved method for carrying out reactions between hydrogen and oxygen gaseous reactants at a reaction rate which is usefully slowed from explosive velocity.

Another object of the present invention is the provision of an improved method of controlling the rate of reaction between hydrogen and oxygen gaseous reactants.

Another object of the present invention is the provision of an improved method for controlling the rate of reaction between hydrogen and oxygen gaseous reactants by use of a Contacogen.

Other objects and advantages of the present invention will be apparent from the following description and the appended claims.

DETAILED DESCRIPTION OF THE INVENTION

The type of reactions with which the present invention is concerned are those involving two gaseous reactants which are brought into controlled contact with a Contacogen in a liquid phase, the contact between the reactants being primarily at an interface of the Contacogen and the gases and the liquid. The controlled contact is an important aspect of the present invention.

One typical reaction which can be controlled by the present invention is that between hydrogen gas and oxygen gas. As is well known, hydrogen gas reacts with oxygen gas in a strongly exothermic reaction, explosive in nature. It is for this reason that special precautions must be taken in handling mixtures of hydrogen and oxygen gases. With these and other highly reactive gases, it would be advantageous to provide for control of the rate of reaction. Rate reducing procedures, such as use of water vapor or a liquid such as water and the like have the effect of reducing the rate to an insignificantly low level.

By the present invention, gaseous oxygen and hydrogen are reacted in the presence of a Contacogen and an aqueous medium to form water, the rate of reaction being significantly faster in an aqueous medium and a Contacogen than in the presence of an aqueous medium without Contacogen. Hydrogen and oxygen gases were introduced into a reaction chamber at ambient temperature and pressure, at controlled rates, and the effluent gas analyzed for oxygen content. In some tests, air was used rather than pure oxygen. In one reactor, air was introduced at a rate of 11.15 cc/min. and hydrogen at a rate of 6.1 cc/min. The reactor was packed with granular carbon without any wetproofing agent. The output gas after equilibrium had an oxygen content of 17.8% as determined by a polarographic gas oxygen meter.

1. Using the same flow rates, supra, and essentially the same reactor, a Contacogen of PTFE wetproofed granular carbon containing platinum inclusions (by surface treatment with 5% by weight of chloroplatinic acid) was used. The Contacogen was maintained in a fixed static bed. The percentage of oxygen in the effluent gas was reduced to 10% and considerable heat was generated. The test was discontinued to avoid an explosion.
2. The same reactor and Contacogen as above were used but the Contacogen was wet (not flooded) with distilled water. The output gas analysis showed about 1.5% oxygen after equilibrium conditions were reached.

Other Contacogen materials used included platinized titanium sponge prepared as follows: The sponge was boiled in 5% oxalic acid and 5% platinum chloride based on the weight of the sponge. During boiling a yellow liquor was found, and after the 15 minutes boiling, the yellow liquor was poured off. The sponge was then washed with distilled water several times and added to a 22% PTFE solids emulsion, the amount of emulsion solids being 22% based on the weight of the sponge. The water was evaporated and the material dried at 100° C. over night. In a separate preparation, the same steps were carried out except that the sponge was not wetproofed with PTFE.

Each material was used in a reactor, without any water and in each case the reaction between hydrogen gas and oxygen was evident because of the high output of heat. In some cases explosions occurred. The same materials were then wet with water and the wetproofed material was effective in bringing about reaction, the oxygen content dropping from 15% to 3% after thirty minutes continuous operation to reach a steady state at a combined hydrogen-air gas input of 17 cc/min. (11 cc/min. air and 6 cc/min. hydrogen). The non-wetproofed material was ineffective in bringing about a detectable reaction.

The reaction between hydrogen and oxygen is of importance in various segments of the technology. For example, atomic reactors of the "Boiling Water" type produce an off-gas normally made up of 60% hydrogen, 30% oxygen and 10% air by volume. The usual treatment of these off gases involves absorption of the gases on a carbon bed to provide a time delay for deactivation of any radioactive contaminants. In order to prevent explosion on the carbon bed, the hydrogen gas content must be reduced. This is done in a "catalytic recombiner" in which the gas stream is diluted with steam to 4% $H_2$ content, then heated to drive off any liquid between and reaction of 95% of the $H_2$. The gases are then condensed, and again diluted with steam and reheated and passed over a second stage to achieve removal of 99% of the hydrogen gas.

The present invention when applied to the above system or to Pressure Water Reactors vastly simplifies the treatment of off reactor gases in that the hydrogen and oxygen can be passed through a reactor packed with Contacogen maintained in a static condition and wetted, but not flooded, with a liquid such as water. By use of water or a liquid phase, the temperature of the Contacogen reactor is controlled, as the above data indicates, and the rate of reaction is sufficiently fast to be of practical use.

The present invention may also be used to treat gases produced by electrochemical processes, e.g., (a) Chlorate production from aqueous sodium chloride;
(b) Chlor-alkali cells for production of chlorine and sodium hydroxide;
(c) Conversion of sodium or potassium ferrocyanide in aqueous solution to the corresponding ferricyanide;
(d) Conversion of aqueous sodium sulfide to sodium polysulfide and alkali;
(e) Conversion of aqueous systems to produce high purity oxygen; and
(f) Conversion of sodium thiosulfate to sodium sulfate.

Each of the above systems is characterized by the formation of a gas at one electrode, usually hydrogen at the cathode, and sometimes oxygen or chlorine or both at the anode. In the usual case, the gases at the anode are the desired products whereas the gas at the cathode is hydrogen and presents problems due to explosion and the like. For further details, reference is made to Ser. No. 252,285, filed May 11, 1972, supra.

While the methods herein described constitute preferred embodiments of the invention, it is to be understood that the invention is not limited to these precise methods, and that changes may be made therein without departing from the scope of the invention which is defined in the appended claims.

What is claimed is:

1. The method for promoting the reaction between hydrogen gas and oxygen gas in the presence of liquid water to produce a water reaction product consisting essentially of the steps of:

(a) providing a fixed bed of platinized particles, said platinized particles having been partially encapsulated with 0.1%–100% of polytetrafluoroethylene by weight,
(b) bringing said hydrogen gas into contact with said liquid water and said platinized particles, and
(c) bringing said oxygen gas into contact with said liquid water and said hydrogen gas and said platinized particles to effect reduction oxidation between said hydrogen and oxygen at said platinized paticles and in the presence of said liquid water to produce the water reaction product.

2. The method of claim 1 wherein said particles are carbon particles having a particle size of between 9 millimicrons and 1 inch and having a surface area of from 3 square meters per gram to in excess of 950 square meters per gram (BET).

3. The method of claim 1 wherein said particles are titanium sponge particles.